United States Patent
Oroskar et al.

(10) Patent No.: US 7,544,293 B2
(45) Date of Patent: Jun. 9, 2009

(54) VALVE AND PROCESS FOR INTERRUPTED CONTINUOUS FLOW CHROMATOGRAPHY

(75) Inventors: Anil Rajaram Oroskar, Oak Brook, IL (US); Saurabh Paresh Parikh, Villa Park, IL (US); Asha Anil Oroskar, Oak Brook, IL (US); Kenneth U. Johnson, Stoughton, WI (US); Anthony Joseph Escarcega, Madison, WI (US)

(73) Assignee: SEMBA Inc., Fitchburg, WI (US)

( * ) Notice: Subject to any disclaimer, the term of this patent is extended or adjusted under 35 U.S.C. 154(b) by 738 days.

(21) Appl. No.: 11/234,798

(22) Filed: Sep. 26, 2005

(65) Prior Publication Data

US 2007/0068873 A1    Mar. 29, 2007

(51) Int. Cl.
  *B01D 15/08*    (2006.01)
(52) U.S. Cl. .................. 210/198.2; 210/424; 210/659; 137/625.4
(58) Field of Classification Search ............. 210/198.2, 210/424, 659; 137/312, 601.05, 625.15, 137/625.17, 625.4
  See application file for complete search history.

(56) References Cited

U.S. PATENT DOCUMENTS

| | | | |
|---|---|---|---|
| 2,985,589 A | 5/1961 | Broughton et al. |
| 4,182,633 A | 1/1980 | Ishikawa et al. |
| 4,267,054 A | 5/1981 | Yoritomi et al. |
| 4,423,109 A | 12/1983 | Greenman et al. |
| 4,434,051 A | 2/1984 | Golem |
| 4,511,150 A | 4/1985 | Séguenot |
| 4,522,726 A | 6/1985 | Berry et al. |
| 4,574,840 A | 3/1986 | Schumann et al. |
| 4,614,204 A | 9/1986 | Dolejs |
| 4,614,205 A | 9/1986 | Oroskar |
| 4,625,763 A | 12/1986 | Schick et al. |
| 4,632,149 A | 12/1986 | Oroskar et al. |
| 4,633,904 A | 1/1987 | Schumann et al. |
| 4,638,976 A | 1/1987 | Souplet et al. |
| 4,705,627 A | 11/1987 | Miwa et al. |
| 4,764,276 A | 8/1988 | Berry et al. |
| 4,808,317 A | 2/1989 | Berry et al. |
| 4,923,616 A | 5/1990 | Hirata et al. |
| 4,990,259 A | 2/1991 | Kearney et al. |
| 5,102,553 A | 4/1992 | Kearney et al. |
| 5,122,275 A | 6/1992 | Rasche |
| 5,156,736 A | 10/1992 | Schoenrock |
| 5,203,368 A | 4/1993 | Barstow et al. |

(Continued)

OTHER PUBLICATIONS

International Search Report for International Application No. PCT/US2007/019126, dated Mar. 4, 2008.

(Continued)

*Primary Examiner*—Ernest G. Therkorn
(74) *Attorney, Agent, or Firm*—Kent Barta S.C.

(57) ABSTRACT

A unique valve assembly for simulated bed moving chromatography employs a combination of pressure compatible sealable materials that permit minimal frictional interaction between moving parts, ensures alignment of parts, and provides a method for conducting SMB countercurrent chromatography on a small scale, in which purity and separation efficiency are enhanced. Machine designs are disclosed which embody the SMB concepts. Finally, a quick disconnect connector and adaptor is provided for mounting chromatographic columns in an SMB device. Demonstration of this system in a fructose-glucose isomer separation with purity-recovery trade-off for this device is also presented.

6 Claims, 16 Drawing Sheets

U.S. PATENT DOCUMENTS

| | | | |
|---|---|---|---|
| 5,395,879 A * | 3/1995 | Murray | 524/571 |
| 5,456,825 A | 10/1995 | Negawa et al. | |
| 5,457,260 A | 10/1995 | Holt | |
| 5,465,748 A | 11/1995 | Bowers | |
| 5,518,625 A | 5/1996 | Priegnitz et al. | |
| 5,556,546 A | 9/1996 | Tanimura et al. | |
| 5,565,104 A | 10/1996 | Priegnitz | |
| 5,595,665 A | 1/1997 | Noe | |
| 5,618,972 A | 4/1997 | Funk et al. | |
| 5,635,072 A | 6/1997 | Moran | |
| 5,645,729 A | 7/1997 | Priegnitz et al. | |
| 5,676,826 A | 10/1997 | Rossiter et al. | |
| 5,685,992 A | 11/1997 | Cohen et al. | |
| 5,705,061 A | 1/1998 | Moran | |
| 5,730,877 A | 3/1998 | Heikkilä | |
| 5,750,820 A | 5/1998 | Wei | |
| 5,770,088 A | 6/1998 | Ikeda et al. | |
| 5,884,777 A | 3/1999 | Pan et al. | |
| 5,912,395 A | 6/1999 | Noe | |
| 6,017,448 A | 1/2000 | Hotier et al. | |
| 6,063,285 A | 5/2000 | Hotier et al. | |
| 6,068,770 A | 5/2000 | Niermeyer et al. | |
| 6,096,218 A | 8/2000 | Hauck et al. | |
| 6,099,736 A | 8/2000 | Hotier | |
| 6,123,849 A | 9/2000 | Purdom | |
| 6,146,537 A | 11/2000 | Ferschneider et al. | |
| 6,149,874 A | 11/2000 | Hotier | |
| 6,162,949 A | 12/2000 | Gattuso | |
| 6,196,266 B1 | 3/2001 | Breda | |
| 6,200,390 B1 | 3/2001 | Kearney et al. | |
| 6,217,774 B1 | 4/2001 | Nagamatsu et al. | |
| 6,224,776 B1 | 5/2001 | Heikkilä et al. | |
| 6,261,458 B1 | 7/2001 | Callebert et al. | |
| 6,284,134 B1 | 9/2001 | Ferschneider et al. | |
| 6,284,200 B1 | 9/2001 | Hotier | |
| 6,348,637 B1 | 2/2002 | Harris | |
| 6,379,554 B1 | 4/2002 | Kearney et al. | |
| 6,402,959 B1 | 6/2002 | Dessapt et al. | |
| 6,455,736 B1 | 9/2002 | Zinnen et al. | |
| 6,458,955 B1 | 10/2002 | Gattuso | |
| 6,508,938 B2 | 1/2003 | Maiefski et al. | |
| 6,544,413 B1 | 4/2003 | Nagamatsu et al. | |
| 6,548,662 B1 | 4/2003 | Ohsaki et al. | |
| 6,551,512 B1 | 4/2003 | Britsch et al. | |
| 6,572,775 B2 | 6/2003 | Heikkilä et al. | |
| 6,602,420 B2 | 8/2003 | Kearney et al. | |
| 6,632,200 B2 * | 10/2003 | Potter et al. | 604/247 |
| 6,652,755 B2 | 11/2003 | Ikeda | |
| 6,712,973 B2 | 3/2004 | Adam et al. | |
| 6,719,001 B2 | 4/2004 | Ahlgren et al. | |
| 6,740,243 B2 | 5/2004 | Wankat | |
| 6,752,929 B1 | 6/2004 | Zahr et al. | |
| 6,770,757 B2 | 8/2004 | Paananen et al. | |
| 6,779,557 B2 | 8/2004 | Weiss | |
| 6,783,673 B2 | 8/2004 | Horsman et al. | |
| 6,797,175 B2 | 9/2004 | Hotier | |
| 6,805,799 B2 | 10/2004 | Ma | |
| 6,843,854 B2 | 1/2005 | Farrenburg et al. | |
| 6,875,349 B2 | 4/2005 | Heikkilä et al. | |
| 6,896,811 B2 | 5/2005 | Heikkilä et al. | |
| 6,896,812 B1 | 5/2005 | Frey | |
| 6,951,340 B2 * | 10/2005 | Suzuki et al. | 277/650 |
| 6,979,402 B1 | 12/2005 | Sprague et al. | |
| 2004/0241878 A1 | 12/2004 | Thommes et al. | |
| 2005/0098962 A1 * | 5/2005 | Duclos et al. | 277/628 |
| 2005/0194318 A1 | 9/2005 | Ozbal et al. | |
| 2006/0185419 A1 | 8/2006 | Gamache et al. | |
| 2007/0131615 A1 | 6/2007 | Moran et al. | |
| 2008/0053543 A1 | 3/2008 | Baier et al. | |
| 2008/0053901 A1 | 3/2008 | Mierendorf et al. | |
| 2008/0053917 A1 | 3/2008 | Larson et al. | |

OTHER PUBLICATIONS

International Search Report and Written Opinion for International Application No. PCT/US2006/37232, dated Feb. 6, 2008.

* cited by examiner

Purity vs. Recovery of Cycle time 5 mins, Feed Rate: 160 gm/hr, Desorbent Rate:1818gm/hr

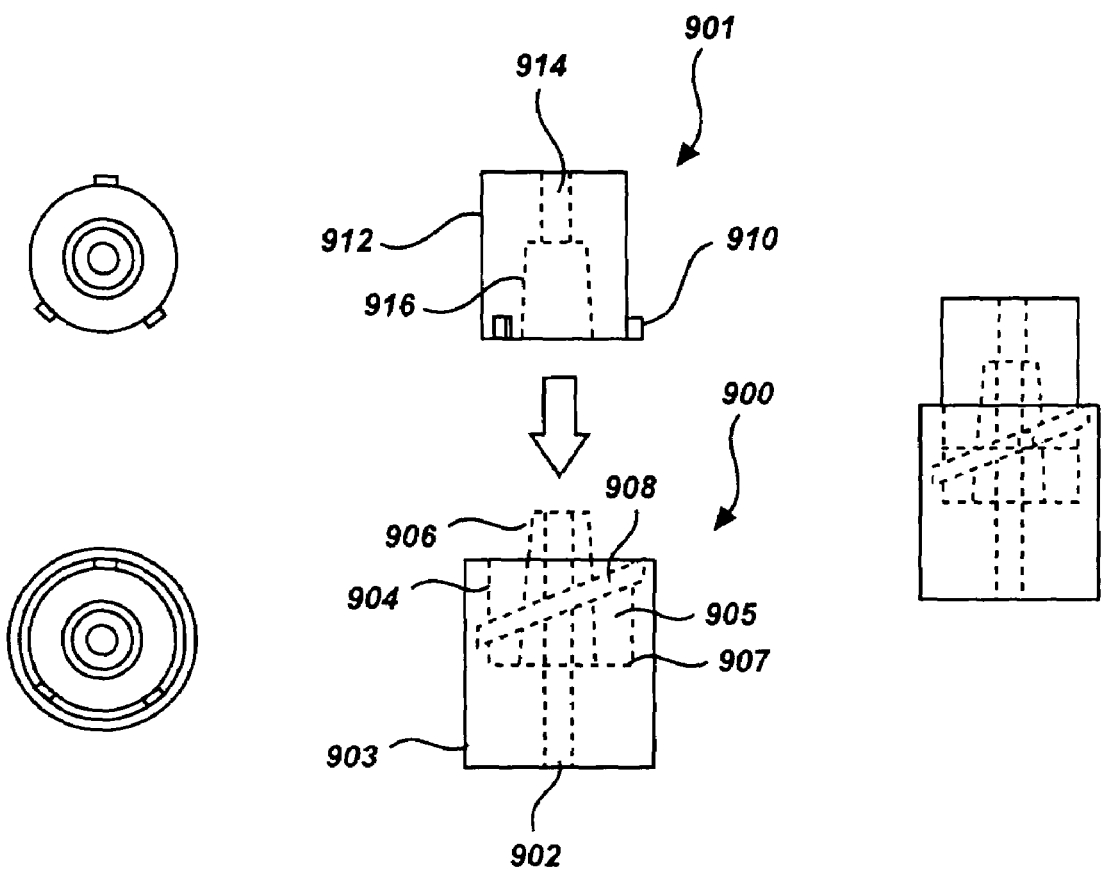
*Fig. 10A*  *Fig. 10B*  *Fig. 10C*

VALVE AND PROCESS FOR INTERRUPTED CONTINUOUS FLOW CHROMATOGRAPHY

FIELD OF THE INVENTION

The present invention relates generally to continuous flow chromatography, and more particularly, to Simulated Moving Bed (SMB) chromatography. The invention provides a novel strategy for small scale separations of liquid components in a stream, and a simplified valve design for directing liquids to appropriate destinations within the system.

BACKGROUND OF THE INVENTION

In typical solid phase chromatography processes, a solution containing a mixture of substances is passed through a bed of adsorbent. One or more of the dissolved substances in the flow has a greater tendency to be adsorbed onto the solid matrix than others. In the case of gel filtration separation is based on molecular weight, with small substances permeating the gel which retards their movement through the gel relative to larger molecules which are excluded from the pores of the gel. In ion exchange chromatography, the principle of separation involves differential interaction with a resin of different molecules according to their charge properties. The resins may consist of a backbone polymer to which selected functional chemical groups are appended. Ionic interactions cause some molecules to bind to the resin, while others pass through the resin bed. Over the years, a large variety of resins and other chromatographic substrates have become commercially available.

Small scale laboratory solid chromatography is generally carried out in a column or cartridge. The column comprises a hollow cylinder with fittings at both ends, the bottom end of the cylinder containing a frit with pores of smaller size than the gel or resin particles to retain the solid substrate in the column. A slurry is poured into the column and the substrate is packed by eluting solution through the column. When a sample containing a mixture of molecules to be separated is applied to the appropriate resin bed, a molecule to be separated binds to the resin, and the unbound components travel through the column and out at the bottom. A desorbent is then eluted which releases the bound molecule, and it too passes through the column. Typically in a laboratory small aliquots of eluted liquid are collected in an automatic fraction collector. Since the column is now filled with desorbent, it must be washed with a starting buffer to regenerate the functional groups on the resin before another sample batch can be applied.

In the laboratory, the batch type chromatography process is satisfactory because many applications are analytical. Even when preparative quantities are recovered, the amounts needed are relatively small, and sufficient reagent is obtainable by one or a few batch runs. However, batch type chromatography is generally unsuitable for large industrial purifications. The time consumed by washing and regeneration of columns is not cost effective. Also, many writers have pointed out that in a batch system, only a fraction of the resin bed is actually in use in each cycle, resulting in production inefficiencies. See U.S. Pat. No. 5,156,736 and U.S. Pat. No. 4,379,751. Finally, batch processes are wasteful of reagents whose only function is to wash and regenerate the column.

Over forty years ago, a new process was developed specifically for large scale industrial purifications. U.S. Pat. No. 2,985,589 disclosed a chromatography system involving a separation tower divided into a number of individual separation beds. These beds are connected in series, and the outlet at the bottom most bed is connected to a pump that returned flow in a continuous loop to the upper most bed. The inlet apparatus for each bed has a port connected to a downward flowing conduit. The conduits terminate in fittings attached to a rotary valve designed to control both ingress and egress of liquids into or from the inlets to each individual bed. The system is called Simulated Moving Bed (SMB) chromatography because the beds appear to be moving in a direction countercurrent to the direction of flow.

FIG. 1 is a schematic depicting the principle of SMB chromatography. The figure shows eight individual chromatography columns arranged in series bottom to top in a continuous loop. A pump is represented by an oval at the left. Also, two inlets marked D and F are shown, as well as two outlets E and R. F stands for feed, and it is at this point fresh feedstock containing the mixture of substances to be separated is added to the system. D denotes the desorbent inlet. At this point the solution is added containing an agent releasing species of molecule which was previously bound to the solid substrate. R stands for raffinate, the term given to the flow from the system containing all of the molecular species which did not bind to the column, and E is the exit line carrying away previously bound species, released by the desorbate.

FIG. 2 is a graphical representation materials status of distribution at one point in time. The graph defines four zones according to the predominant function occurring in twelve columns. In this illustration, there are six columns in the series. In zone I, bound species are eluted from the solid substrates by infusion of eluent at a point where the level of unbound species is minimal. Zones II and III. At the point of greatest separation, the raffinate is drawn off, thereby eliminating the unbound species at a point where most of the species with affinity for the solid matrix is already bound. Finally this diagram shows Zone IV, which provides for recycling of eluent. The most common applications involve some type of affinity resin, but SMB can be utilized in molecular weight differentiating subjects as well, as disclosed in U.S. Pat. No. 6,551,512.

Referring again to FIG. 1, in the diagram, feedstock is shown entering column 6, raffinate is removed prior to entry of flow into column 8, desorbent is added to the stream prior to entry of flow to column 2, and extract is removed before entry of flow to column 4. In the next step, however, the inlets and outlets are shifted one position counterclockwise to positions 5, 7, 1, and 3; and so on in successive steps. Thus, there is a substantially continuous inflow of feedstock, and a simultaneous collection of purified extract.

The continuous nature of SMB operation is characterized by very brief flow stoppages during the port switchovers in successive process steps. However, since all input and output conduits briefly stop at the same time, there are no significant pressure drops or surges in the system. Indexing of mechanical rotors is designed to effect rapid switchovers, even on very large industrial machines. Further, strategy in the design of process configuration is largely dictated by the affinity and release characteristics of bound species to the solid substrate, exclusion properties of unbound species, the bed volume required to obtain separation of by-product, and other factors. Where separations involve more than two components, the use of coupled SMB systems may be advantageous, as demonstrated in U.S. Pat. Nos. 6,379,554 and 6,662,420. In the case of the '554 patent, the desired product is removed in the raffinate of the first SMB loop, and further purified in a second loop to separate high molecular compounds, ash content, etc. See also U.S. Pat. No. 6,402,959. A similar system is disclosed in U.S. Pat. No. 5,122,275 in which two interconnected SMB trains of columns alternate, resulting in reduced processing time compared to a single train having twice as many columns.

In over forty years since the '589 patent issued, there have been over 200 patents issued on modifications of SMB disclosing improvements in separation efficiency generally, or in particular applications, enhanced purity and yield in the final products, or reduction in required volume desorbent. For example, in one variation disclosed in U.S. Pat. No. 5,156,736, separations are performed in a single bed preserving the principles of SMB by interposing at various levels in the bed a series of crossectionally functional collecting and distribution means for adding feedstock and recycled process liquid, collecting raffinate, distributing eluent, and recovering extract product. Equilibrium is established in the system by very precise flow and pressure control. In U.S. Pat. No. 5,595,665, flushing apparatus is provided generally comprising a fluid distribution manifold, whereby incoming line fluid will enter an equalization chamber and be removed by a connecting conduit. Contamination by trailing peaks is thereby reduced. Other flushing embodiments are described in U.S. Pat. No. 4,319,929. Another improvement is described in U.S. Pat. No. 6,652,775 for solving the problem of cumulative pressure drops between SMB columns, which greatly prolong the washing process in cleaning the system. The '775 patent discloses washing means which, singly or simultaneously, wash defined units of one or more columns, utilizing the inlet feedstock and desorbent ports; and raffinate and extract outlet ports for ingress and egress of wash solution.

The key to achieving SMB process control, is the valve system which directs flows through the system, and regulates inputs and outputs. The early '589 patent employed a valve capable in any cycle step in the process, of directing feedstock or desorbent into a predetermined chamber, or matching an open inlet port to the conduit rising up to any predetermined chamber. The rest of the valve positions in the rotor were blind, so liquid was thereby forced to flow downward into the next vertical chamber. A more recent valve device having vertical indexing is disclosed in U.S. Pat. No. 6,196,266. The valve assembly indexes horizontally with ports presented in the vertical cylindrical wall of the valve body. However, some patents describe valve systems arranged co-axially, and designed to turn vertically, as in U.S. Pat. No. 4,625,763. Instead of a rotary valve, many SMB systems have been devised that employ sets of individual valves. U.S. Parent No. 4,434,051 discloses three tiers of three way valves to control the four processes flows. Another U.S. Pat. No. 5,635,072 utilizes a set of three valves per chamber, configured so that a continuously operated circulation pump can be eliminated, thereby conserving liquid volume in small, pilot scale system. U.S. Pat. No. 6,544,413 discloses a plural valve device having elements controlling input or output flow to each column in the SMB series. It has the advantage of reducing volume of liquid in the system for very small scale SMB systems.

Valves having a horizontally disposed plane of movement between stator and rotator are essentially of two types, one type in which stator portion is uppermost, and the other in which the stator is bottommost. The stator lowermost configuration was evident especially in the earlier large industrial units in which the columns were much too large to be moved. The rotary valve alone for some of these units (for example, U.S. Pat. No. 3,040,777) occupied an area of 64 sq. feet and weighed over 10 tons. U.S. Pat. No. 6,719,001 is a recent patent. An example of stator elements mounted in upper fixed position is disclosed in U.S. Pat. No. 4,764,276.

A persistent problem in the operation of rotary valves in SMB application is leaks, usually because of a failure of seals in gaskets in the valve assembly. Such sealing elements are prone to wear because of the substantial pressure under which they operate. In the '276 patent just referred to, sealing engagement is provided by the combination of a sealing wear ring and a compressible ring. Force is applied by a hydraulically actuated piston to obtain sealing of the rotating head assembly and its housing.

SUMMARY OF THE INVENTION

Most simulated moving bed (SMB) chromatography systems are designed for large scale industrial applications involving thousands of gallons of feedstock, and tons of final product. Flow in such systems is highly constrained because of the necessity of maintaining continuous flow of large volumes of liquid in each stage of the process. Small scale systems are not nearly so constrained in part because perturbations in flow are more readily tolerated when circulating flow volume is small compared to bed volume in the columns. It is therefore an object of the present invention to interrupt flow in the series at critical points where inflows and outflows from the system to prevent any possible unintended contamination of columns adjacent to the points of fluid ingress or egress, as will become apparent hereafter.

The key to efficiency of SMB in which each column in the series alternately performs a succession of chromatographic functions, is the valving system. The multi-port rotary valve of the present invention is designed for simplicity of construction, ease of assembly and disassembly, and minimization of wear on the moving parts. In one embodiment, the present valve comprises three substantially flat plates, and in a second embodiment four such plates, maintained in alignment. The bottom plate and a rigid plate composed of a fluorocarbon polymer attached to it are mounted on a frame or carousel, and rotate against an interfacing plate. Each of these structures has a plurality of bores arranged in two concentric arrays of equal number corresponding to the number of potential liquid flows with each outflow from one column connected to only one inflow of the next column in succession. The rigid plate has a lapped surface to a flatness tolerance of not greater than 15 microns, and preferably 1-3 microns, and can readily withstand up to 500 psi and 500 ft. lb of torque. All of the bore arrays are arranged to be in unobstructed alignment when the valve components are layered together. Means are provided to apply uniform pressure across the plates so as to attain a hydraulic seal able to withstand pressures of up to 200 psi.

The stationary interfacing plate similarly has two concentric arrays of bores corresponding in alignment to the bores of the first and rigid plates. The outer portions of these bores are partially threaded to receive connectors for attachment of cross-over conduits interconnecting one column to the next in the series. On the undersurface of the interfacing plate each array of bores is surrounded by a continuous concentric recess whose cavities are designed to receive a fabric entrained gasket. The gasket has holes corresponding to the position and size of the bores in the recess that receives it. The gasket is further made of material thicker than the depth of the recesses, so that when the valve components are assembled, the gasket provides not only sealing engagement between the rigid plate and the interfacing plate, but also reduces the coefficient of friction, and correspondingly the area of wear on the moving parts. It is also advantageous that the gasket is held in place mechanically without use of any chemical adhesive, to facilitate periodic replacement.

In a preferred embodiment of the present invention, crossover conduits interconnecting the columns are replaced by channels machined into a fourth top plate. The lower surface of the top plate has a series of grooved recesses arranged radially. Each recess contains a vertical bore, substantially midway between the ends of the groove, and extending to the upper surface of the top plate. If such a bore is plugged, flow in the system passes upward from a conduit connecting the bottom of one column, traverses the communicating channel recess, and proceeds back down to the top of the next column in the series. In open configuration, these bores serve as predetermined inflow or outflow ports for addition of feedstock or desorbent, or removal of raffinate and extract, respectively. The spaced position of these inflow and outflow ports is selected by empirical determination from the purification profiles of the substances to be separated. Sealing means encompass and isolate each such outflow/inflow bore pairs, to prevent leakage and cross-contamination. Such a sealing barrier is typically an O-ring or a gasket partially seated in an oval shaped recess.

A machine for carrying out SMB chromatography on a small scale comprises valve means as hereinabove disclosed, means for rotating the lower plate and upper plate of such valve means while maintaining the interfacing plate thereof stationary, compression means to maintain sealing engagement of the valve means, control means to maintain the valve means in alignment, positioning means to accommodate chromatographic columns to receive correct inflow in a predetermined sequence, means to direct column eluents to predetermined destinations, means to add or remove liquid from the system at predetermined locations, and pump means to ensure liquid flow in a continuous loop through the columns.

More specifically, a machine embodiment for carrying out SMB chromatography comprises an inner support frame anchored fixedly to a rotating shaft extending perpendicularly from a drive train power means with indexing capability, and an outer support frame having a plurality of support pillars of equal height extending vertically. The inner frame has a central aperture of sufficient diameter to admit the shaft. The machine has a central carousel assembly capable of supporting a plurality of chromatographic columns. The carousel contains a plurality of pillars extending vertically anchored in the inner base plate. The carousel is also provided with a yoke plate having a series of apertures to accommodate insertion of a plurality of disposable separation columns, and at least one cutaway section in its body to facilitate passage therethrough of flexible conduits. The yoke plate is secured at a height on the pillars sufficient to accommodate the full length of the columns and their lower fittings. The support pillars of the carousel terminate in attachment to a plate which also serves as the lower plate of the multi-port rotary valve, described above. The rest of the valve components are mounted on the bottom plate.

An upper support plate is joined to the plurality of outer pillars and has a central aperture and bearing means to receive the upper most portion of the central shaft rising vertically from the inner frame base plate. The purpose of the outer frame is to maintain vertical alignment of the shaft and provide overall lateral stability. The central shaft is further characterized in having threads in the portion of shaft between the interfacing plate of the valve assembly and the outer support frame plate, Pressure sufficient to achieve sealing engagement of the valve components is obtained by exerting pressure on the interfacing plate of the valve by compressing a spring disposed between the interfacing plate and a threaded push plate held in place by a lock nut.

In another embodiment of the present invention, chromatographic columns are attached directly to the bottom side of a rotatable first plate by mating threads contained in a column collar to the threads of the threaded bores. A carousel structure is therefore not needed in this embodiment. The machine comprises an inner frame base plate having an upper and a lower surface anchored to a rotatable shaft extending perpendicularly from a drive power train having indexing controls, a plurality of support pillars extending perpendicularly from the upper surface of the frame base plate, and a valve assembly according to the embodiments heretofore described mounted on the support pillars. The machine is provided with an outer support comprising a plurality of pillars extending vertically, and terminating in threaded vertical extensions. The top plate of the valve has bores at the edges thereof, and the plate is of such size and shape that the bores are engage the pillar extension. The pillar extensions are fitted with spring loaded nuts to generate sufficient force to maintain the valve assembly components in liquid sealing engagement.

The method of the present invention can be used in any SMB of generic construction, in which the volume of liquid flow in the system is small enough not to result in large pressure spikes and depressions, or result in other fluid effects such as water hammer, rupture of conduits and fittings, and the like when interrupted at one or more points in the circulation loop for the time a columns remain in one index position. According to the method, flow is interrupted by interrupting means to any one of two positions occurring in a column immediately downstream from either or both of the inflows of feedstock or desorbent, and optionally interrupting the flow to columns upstream of the outflows of raffinate or extract. In practice, such interruption of flow prevents cross-contamination of columns adjacent to inlets and outlets, thereby sharpening the peaks of separation and optimizing recoveries of product. It is especially adaptable to very small SMB systems useful in drug discovery and separation of highly structurally related chemical compounds.

A quick disconnect connector device for facilitating SMB small scale operation comprises a first cylindrical female body portion having an outer surface and an upper substantially vertical cavity bearing a grooved thread of not greater than one turn of the cylinder. The cavity contains a centrally situated tapered nettle member extending upward from the cavity, and has a central communicating bore passing through the entire female portion body. A second cylindrical male portion body has a central bore and a tapered central cavity adapted to mate with the nipple member of the female portion body. The outer surface of the male cylindrical body portion has flange or tab like projections therefrom, mating with and engageable by the grooved thread situated on the inner surface of the female body portion. The angle of taper from the vertical perpendicular for the respective male and female tapered may differ from each other, but by not more than 5 degrees from the vertical, to ensure that in one or less turns of the thread upon the flange projections, a tight seal will be formed between the male and female connector bodies. It will be apparent to those skilled in the art that the central bores of the female and male connector bodies will connect when joined, and thereby provide a communicating liquid channel.

BRIEF DESCRIPTION OF THE DRAWINGS

FIG. 10A, FIG. 10B, and FIG. 10C show graphical results of tests conducted with a device embodiment of the present invention.

DETAILED DESCRIPTION OF THE PREFERRED EMBODIMENTS

Figure 1:
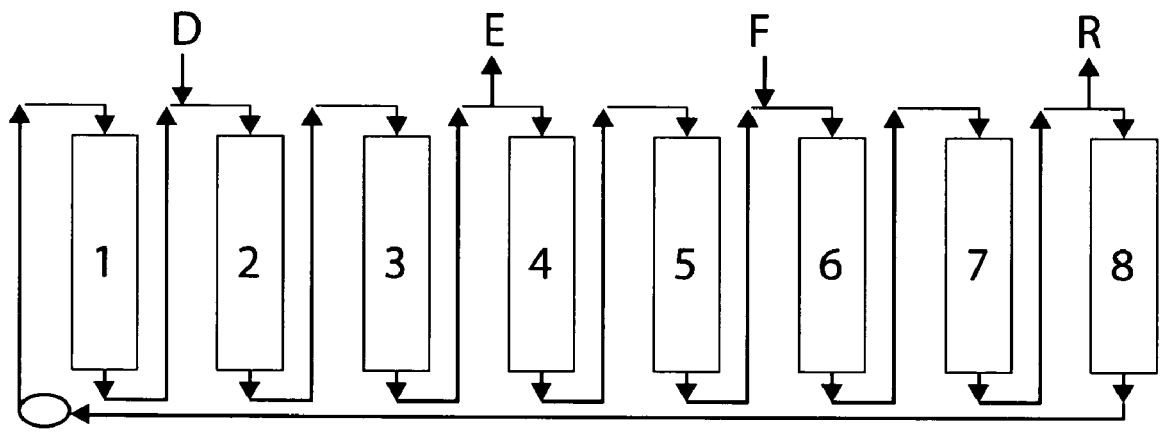
FIG. 1 is a schematic diagram of the operation of a generic SMB device having eight chromatographic columns. The oval represents a pump.
Figure 2:
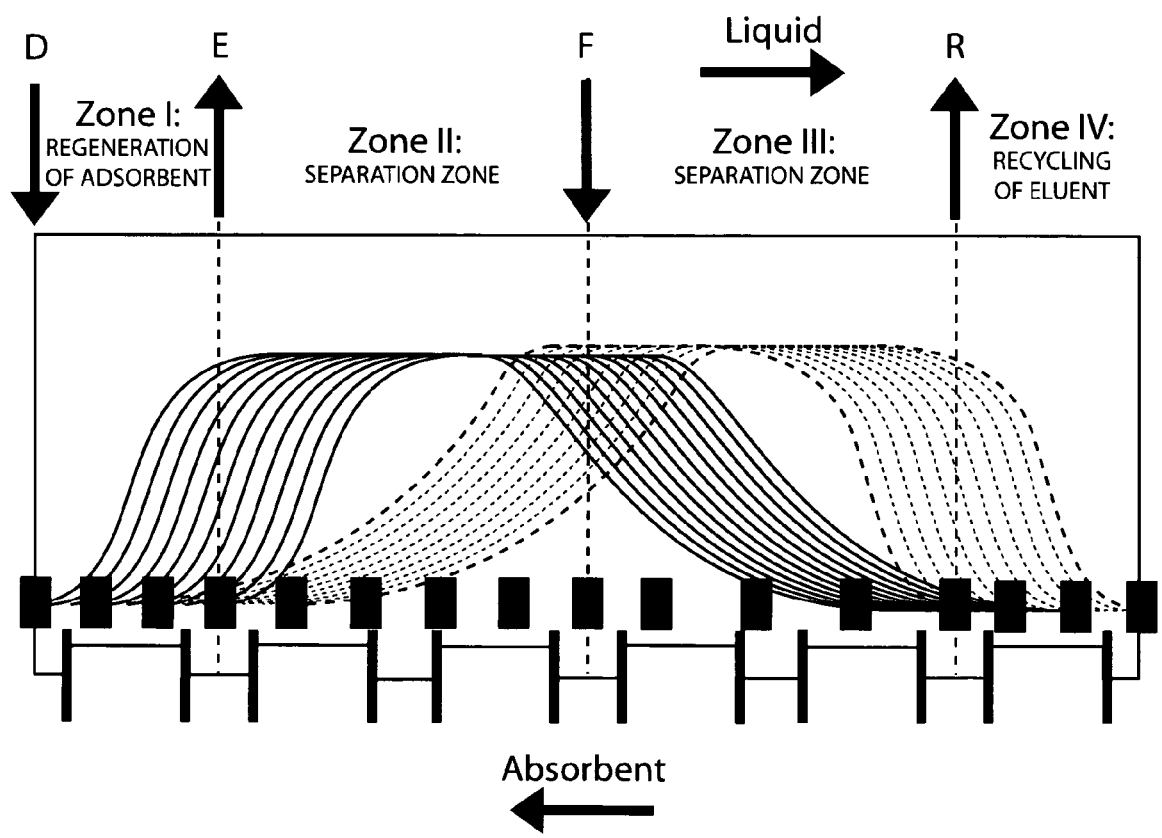
FIG. 2 is a schematic in graphical form, showing the zones of flow in an SMB system.

The principle of continuous flow chromatography relies on the phenomenon of preferential retention on a sorbent of one or more substances in a feedstock mixture, elimination of those substances in the stream not so retained, and release and subsequent recovery of the retained substances. The process involves a number of separate retention beds, interconnected classically by a continuous flow loop. As product is cleared and the sorbent is regenerated, that particular bed becomes the site for addition of more feedstock. FIG. 1 illustrates the process at one particular point in time, and FIG. 2 diagrams the dynamics of flow. The chemical properties of the substances to be separated dictates the type of sorbent used, the number of columns in each zone of the cycle, and the positions of the inlet and outlet. Determination of these parameters is largely empirical.

In large-scale industrial processes, equipment is dedicated to a particular separation, and once the configuration of process parameters is established, it is maintained indefinitely. In the laboratory, however, versatility and ease of changing process parameters is highly advantageous. There is a growing need for research laboratories to have available the means to produce preparative quantities of drugs, biologics, and chemical intermediates sufficient for animal studies, crystallography, invitro studies, and even limited clinical trials. The present invention combines versatility of operation with efficiency in adapting SMB chromatography to small scale preparative separations.

Figure 3A:
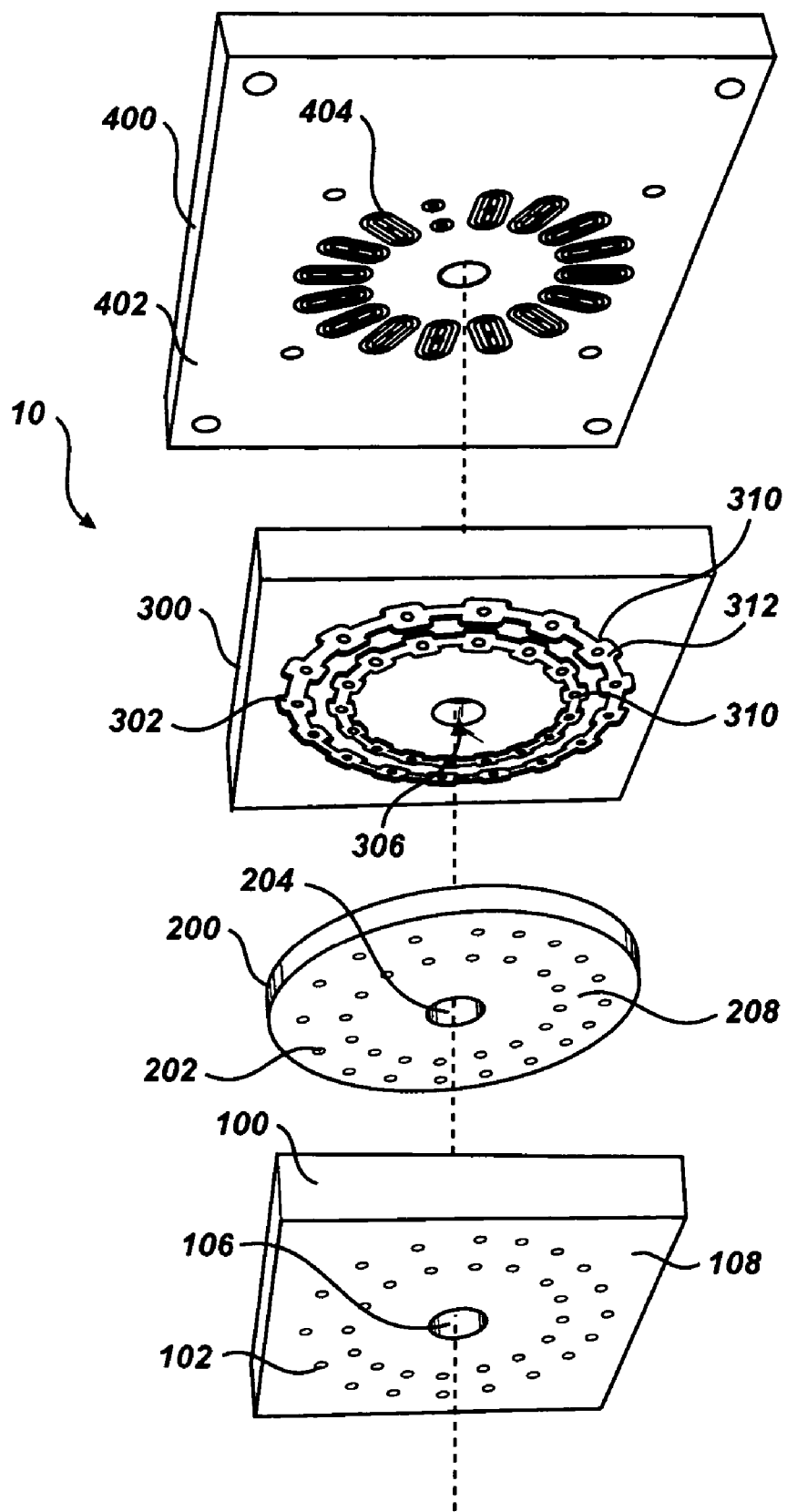
FIG. 3A is an upward facing perspective view of the valve components in exploded view.
Figure 3B:
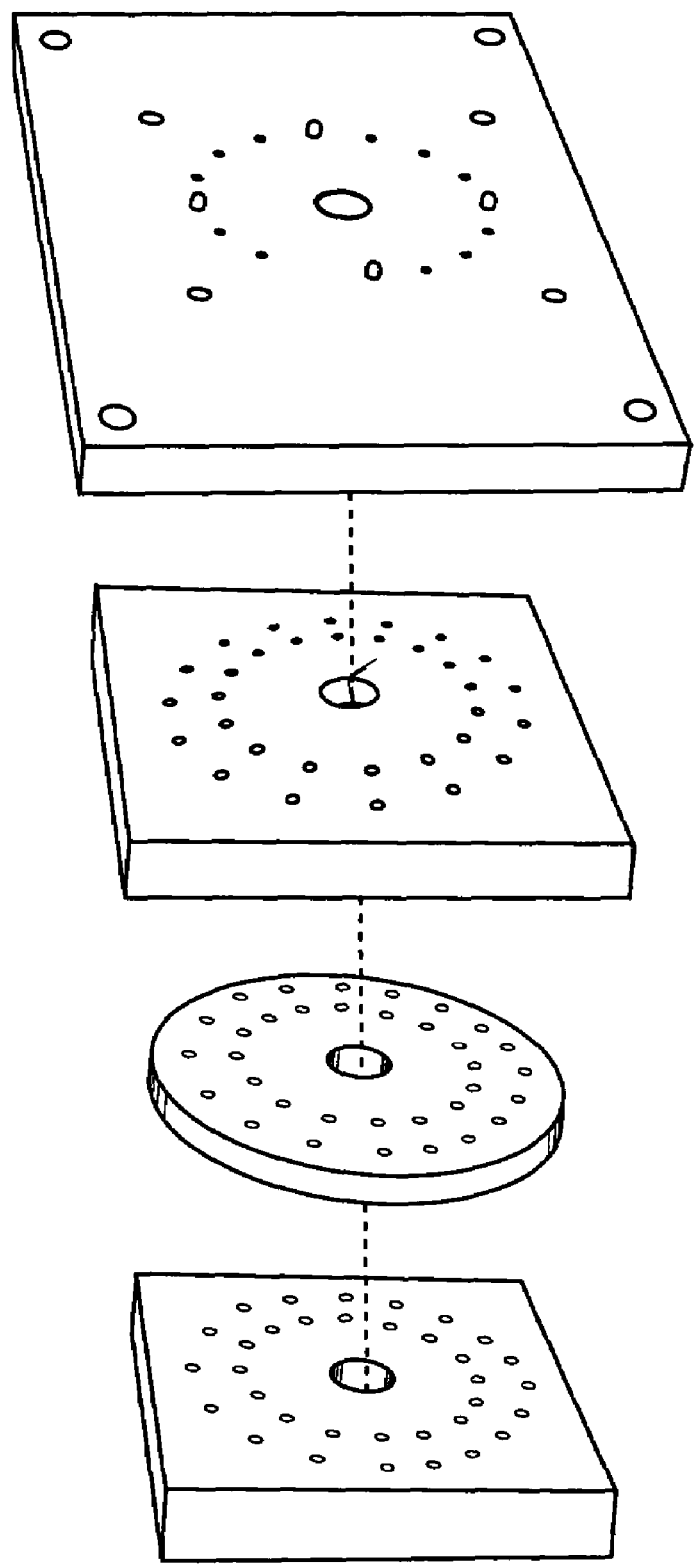
FIG. 3B is a downward perspective drawing of the same component also in exploded view.

In SMB chromatography, a valving system is crucial to ensuring the systematic predetermined regulation of flows to a plurality of sorbent beds. FIGS. 3a and 3b illustrate the structure of the principal components of the present valve in two embodiments in relation to their operating configuration. FIG. 3a is an exploded downward facing view of the lower surfaces of the components, and FIG. 3b is an exploded upward facing view of the essential component features of a multi-port rotary valve generally designated 10. In one embodiment, the valve assembly comprises a rotatable first plate 100, a rigid plate composed of a fluorocarbon polymer 200, and a stationary interfacing plate 300. In a second preferred embodiment, a fourth component top plate 400 is added. The rotatable first plate 100 is joined to the rigid plate 200 so that the two plates rotate synchronously. Immobilization of the rigid plate upon the rotatable plate may be mechanical, provided that screw or bolt heads are countersunk below the surface of the rigid plate. The preferred method of immobilization is by chemical bonding with a conventional adhesive, so as to avoid any potential distortion of the rigid plate surface, which is critical to operation of the valve. In the figures, the first plate and rigid plates are depicted as square and round respectively; however, these shapes are selected for ease of manufacture only, and may be of any desired shape not hindering rotation.

With the exception of the rigid fluorocarbon polymer plate, the valve components can most conveniently and inexpensively be machined from schedule 314 or 316 stainless steel. However, a high density plastic such as polyethylene or polypropylene, anodized aluminum, or titanium alloys may also be utilized. The rigid plate is preferably machined from common dense grades of fluorocarbon polymers sold under the tradename Teflon™, and selected from the group consisting of ethylene tetrafluoroethylene (PTFE), ethylene chlorotrifluoroethylene (ETFE), and polychlorotrifluoroethylene PCTFE), having high hydrophobicity and resistance to deformation up to pressures of about 500 psi.

One very important aspect of the rigid plate manufacture, is the proper preparation of the upper surface which rotates in contact with the interfacing plate 300. Treatments such as fine grinding with immobilized abrasives are not adequate to produce a flat, uniform surface that will not leak. In the preferred method of manufacture, the rigid plate is lapped to a tolerance of not greater than 15 microns, and preferably about 1-5 microns. This means the deviation between highest and lowest points on the surface is preferably 1-5 microns. Great care must also be taken not to scratch the surface when assembling, disassembling, and cleaning the device.

Referring again to FIGS. 3a and b, the figures depict the first plate 100 and rigid plate 200 having a plurality of bores extending through the entire thickness of the plates. Bores exemplified by 102 and 202, are arranged concentrically in two arrays of equal number. The bores in the first plate 100 are preferably partially threaded on a bottom portion to engage thread compatible fittings, or in the case of one embodiment of the invention, a disposable column, the loading end of which has a threaded collar or adapter. Partial threading is preferred so that less residual liquid is retained in the bore space during successive indexed steps in the process. The figures also depict the bores in alignment, the two arrays being distributed equidistantly each array in the first plate 100 being superimposable to the like array in the rigid plate 200. The number of bores in each array is equal to the number of chromatographic columns in the system. Some SMB systems operate with as few as four columns or beds, or as many as twenty four. The one depicted herein has sixteen columns, which is well suited to many small scale separations. The first plate 100 and rigid plate 200 also have central apertures 106 and 206.

Figure 5A:
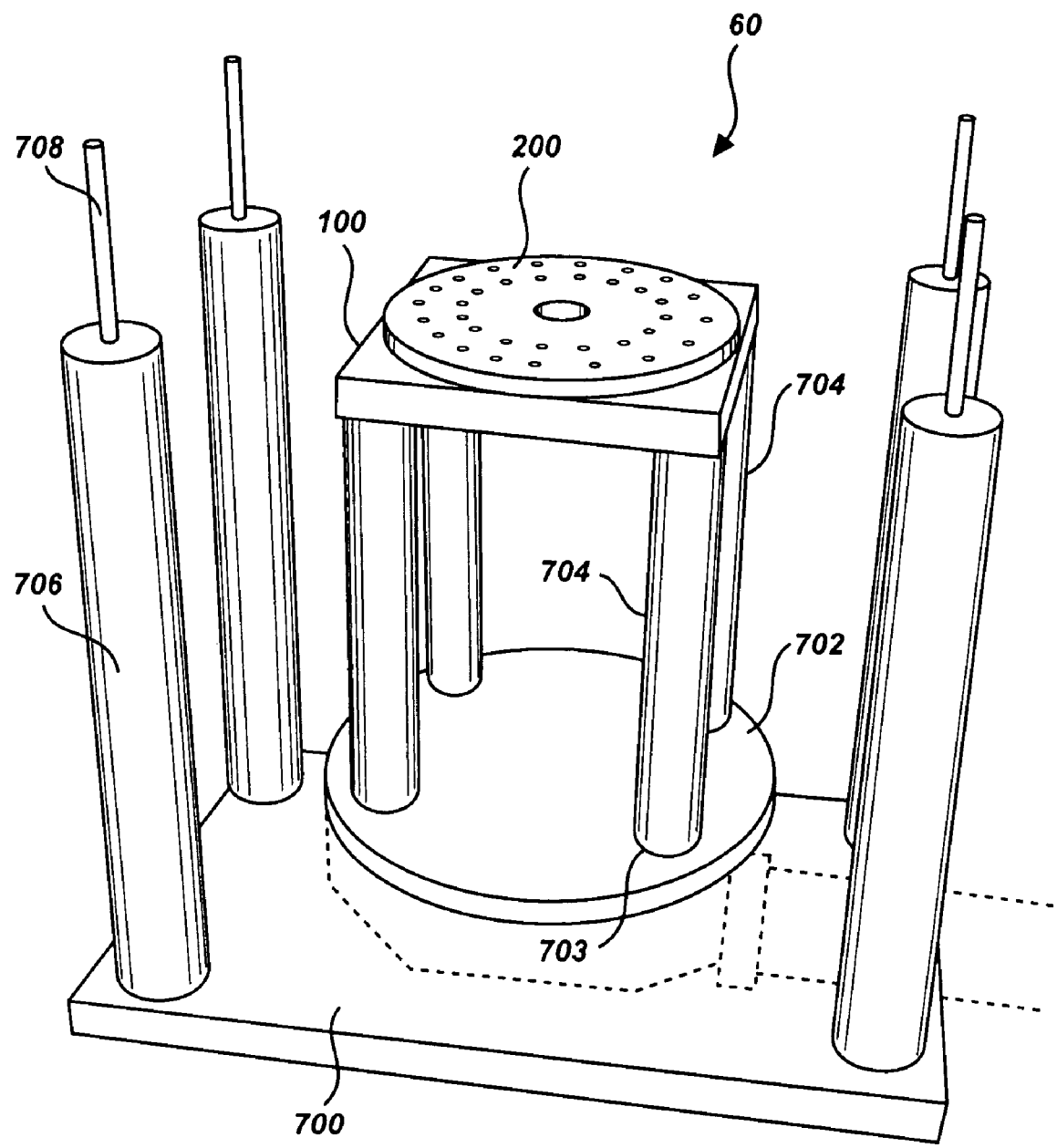
FIG. 5A is a perspective view of the frame, and rotating apparatus of the instant valve.

FIG. 3a shows an exploded view of the valve assembly 10 including an interfacing plate 300, which in operation, is held stationary, as hereafter more fully described. Two recesses 310 and 312, machined into the lower surface 308 of the interfacing plate 300 and extend concentrically and continuously in a circle to provide cavities adapted to receive gaskets of accommodating size and shape. As shown in FIG. 5a, the gaskets 314 are made of a material thicker than the depth of the recess cavities, so that the pressure bearing surface contact between the rigid plate 200 and the interfacing plate 300 is limited to the surface area of the exposed gasket, thus greatly minimizing the coefficient of friction in the relative movement of the plates. The gaskets and recesses adapted to receive them encompass the bores 302 substantially symmetrically at the center of each gasket lobe 318. In FIG. 5*a* the gasket shape is depicted as rectangular radial projections 320 towards and away from the center of the interfacing plate 300 around each bore 302, but the recesses and corresponding gaskets could assume other geometric shapes, so long as the resistance provided at the trailing edge of the recess cavities relative to the forward movement of the valve is sufficient to overcome deformation, tearing, or displacement of the gasket.

The selection of gasket material is crucial to the operation of the valve. Table 1 is a test grid of the various gasket materials that were examined in the valve application.

TABLE 1

| Cat. Number* | Description | Outcome |
| --- | --- | --- |
| 9473K14 | Viton Sheet & flange Gasket ⅛" | Failed |
| 8392K16 | Gor-Tex Rigid Sheet Gasket ⅛" | Failed |
| 13015K57 | Compressed Carbon/Buna-N Sheet ⅛" | Failed |
| 1063T24 | Virgin-PTFE Sheet Gasket ⅛" | Failed |
| 8602K26 | Filled PTFE Sheet Gasket silica filled | Failed |
| 9499K45 | Value Seal Expanded-PTFE Gasket ⅛" | Failed |
| 8635K585 | Commercial-strength Buna-N rubber | Failed |
| 86795K25 | White FDA Buna-N rubber 3/16" | Failed |
| 86715K425 | High strength Buna-N rubber 3/16" | Failed |
| 86215K15 | Weather/Chemical resistant Santoprene | Failed |
| 8632K65 | 70A Durometer Silicone rubber 3/16" | Failed |
| 8617K43 | Fabric reinforced SBR rubber sheet ⅛" | Passed |

*all test materials obtained through McMaster-Carr (a major U.S. distributor of industrial material).

The pass fail criterion was simply whether or not the valve leaked after several hours of continuous use. Only the last one had sufficient stability and durability to pass the test. The gasket material suitable for use in the present invention is selected from a group of polyester fabric mesh entrained synthetic rubber products having a chemical composition of styrene butadiene or a neoprene blend, and a tensile strength of 300-500 psi (strengths are listed as psi). One further advantage of the preferred gasket material is that it retains stability without the use of adhesives to cement into the gasket cavities. Hence, gaskets are easily removed and replaced, without the need for adhesive solvents.

Figure 5B:
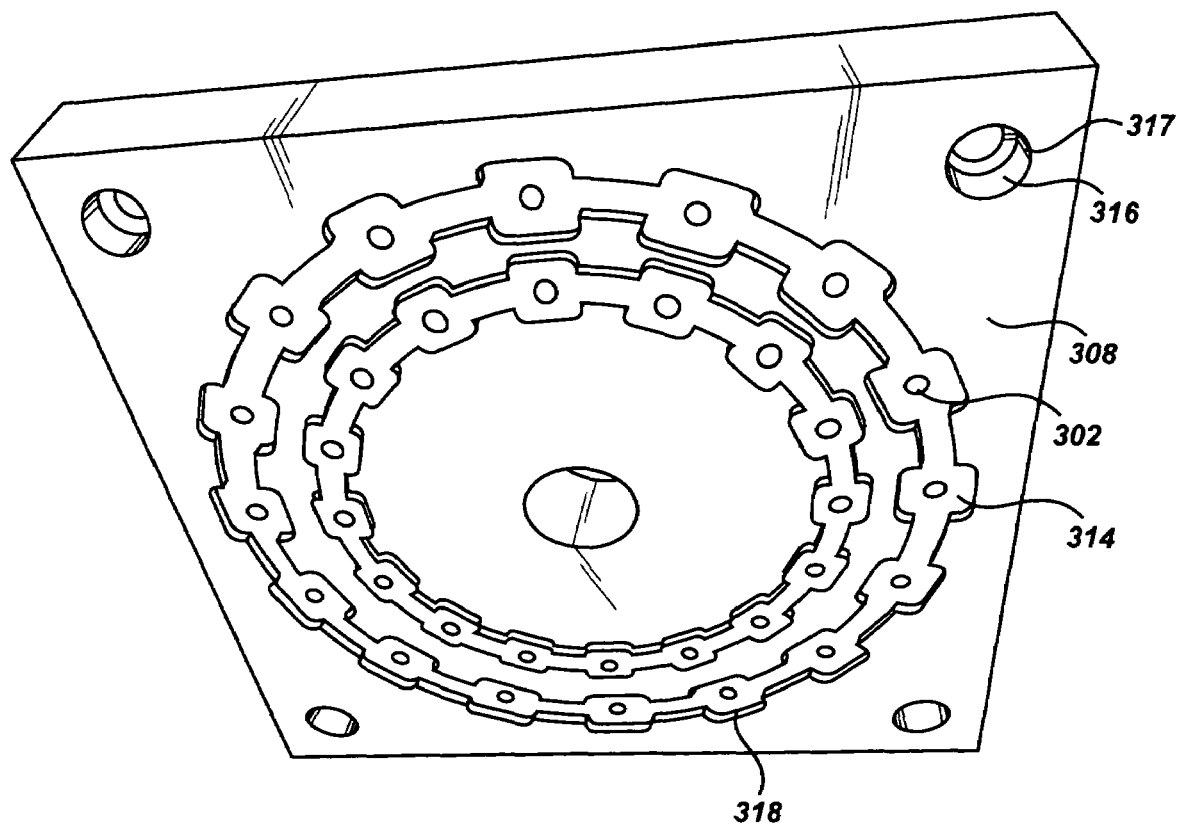
FIG. 5B is a perspective view of the key inventive features of the stationary interfacing plate.
Figure 5C:
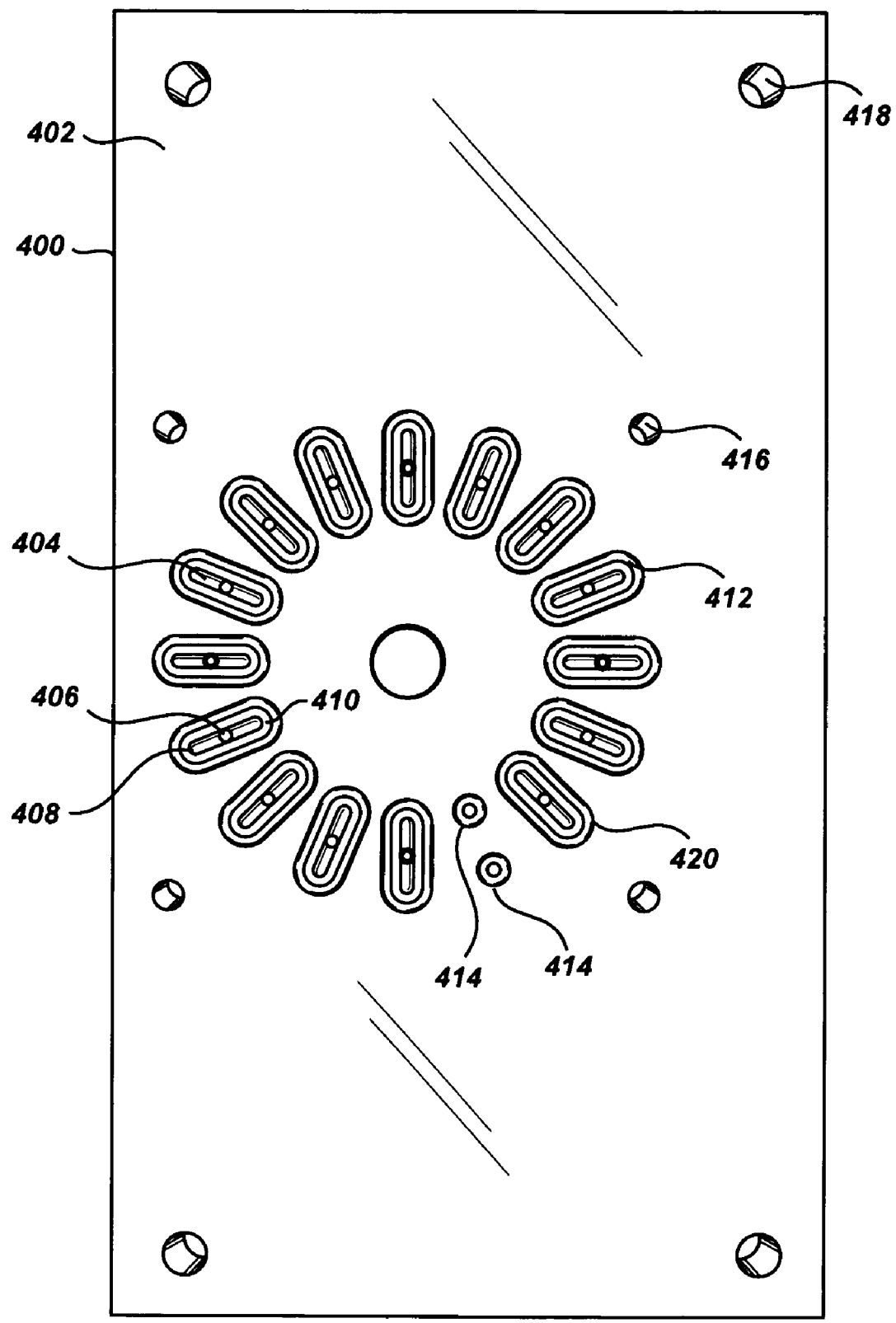
FIG. 5C is a planar view of the top plate lower surface.
Figure 5D:
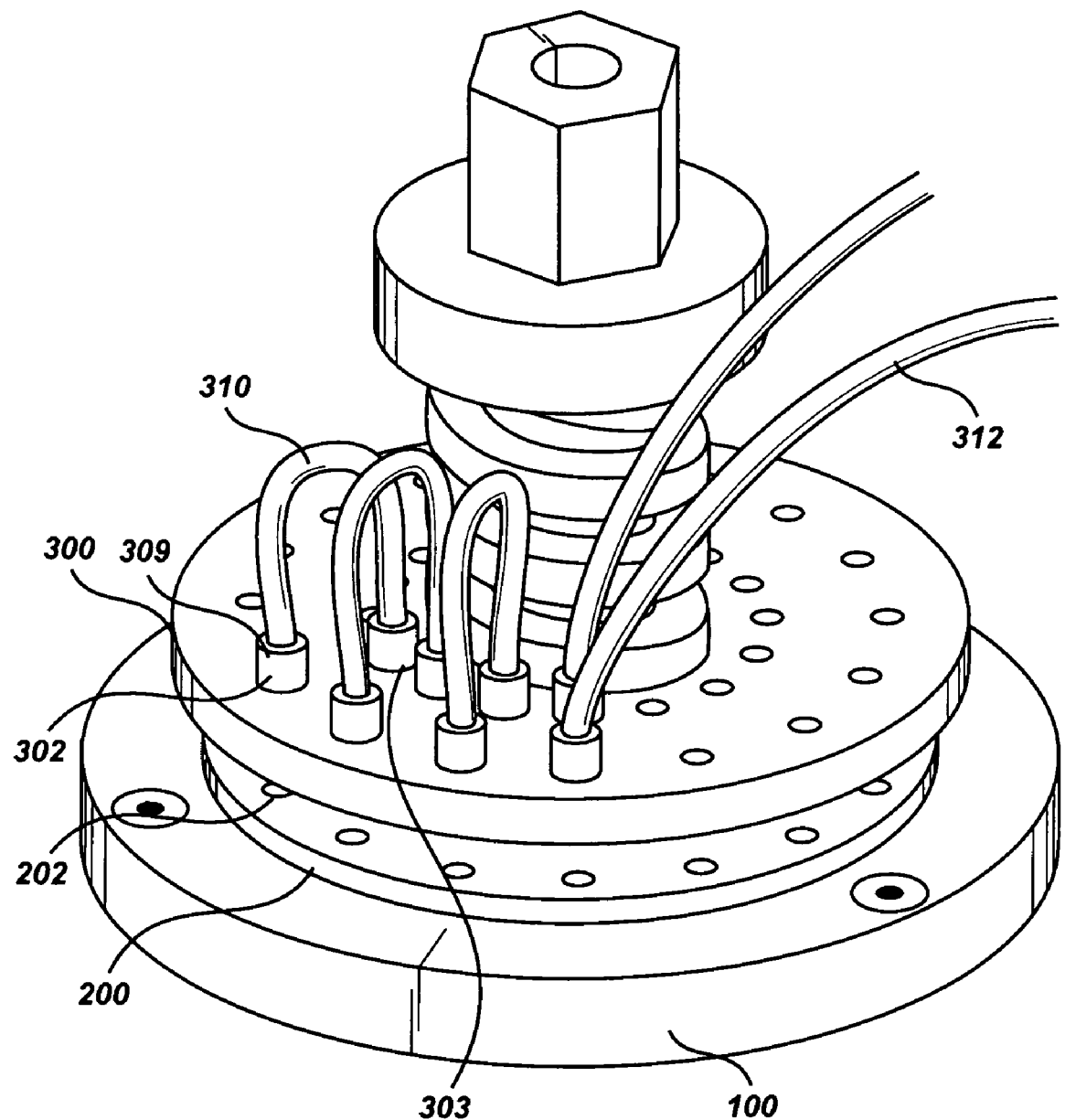
FIG. 5D is a perspective view of the valve assembly and cross-over liquid transfer means in certain embodiments.

Referring to the flow diagram for SMB depicted in FIG. 1, it is apparent that to form a continuous flow loop, it is necessary that the liquid eluting from the base of one column be loaded onto the top of the next column in succession, and that inflows and outflows must occur in succession at each column position, in a continuous loop of flow maintained by an inline pump. In the preferred embodiments of the present invention all inputs to columns are assigned to the outer array bores, and column outputs are assigned to the inner array of bores (although the assignment could be reversed, or otherwise changed in sequence). If any particular column is connected via a conduit to an arbitrarily assigned input on the outer array, its output would be connected to the input of the next column, and so on. Referring to FIG. 3*b*, it will be apparent that when the valve is in aligned index position, an input flowing through aligned bores 102, 202, and 302, must connect to aligned output bores 103, 203, and 303 to carry liquid through that portion of the loop. Referring to FIG. 5*d*, the first plate 100, rigid plate 200, and stationary interfacing plate 300 are shown in partially exploded perspective view. Liquid flowing upward from bore 303 if transferred to bore 202 via a crossover loop 310 attached to bores by a connector 309, and so on, except at positions where feedstock and desorbent are added to the flow, or raffinate and extract is removed from it. Such a inflow/outflow conduit is illustrated as a flow conduit 312.

Figure 4:
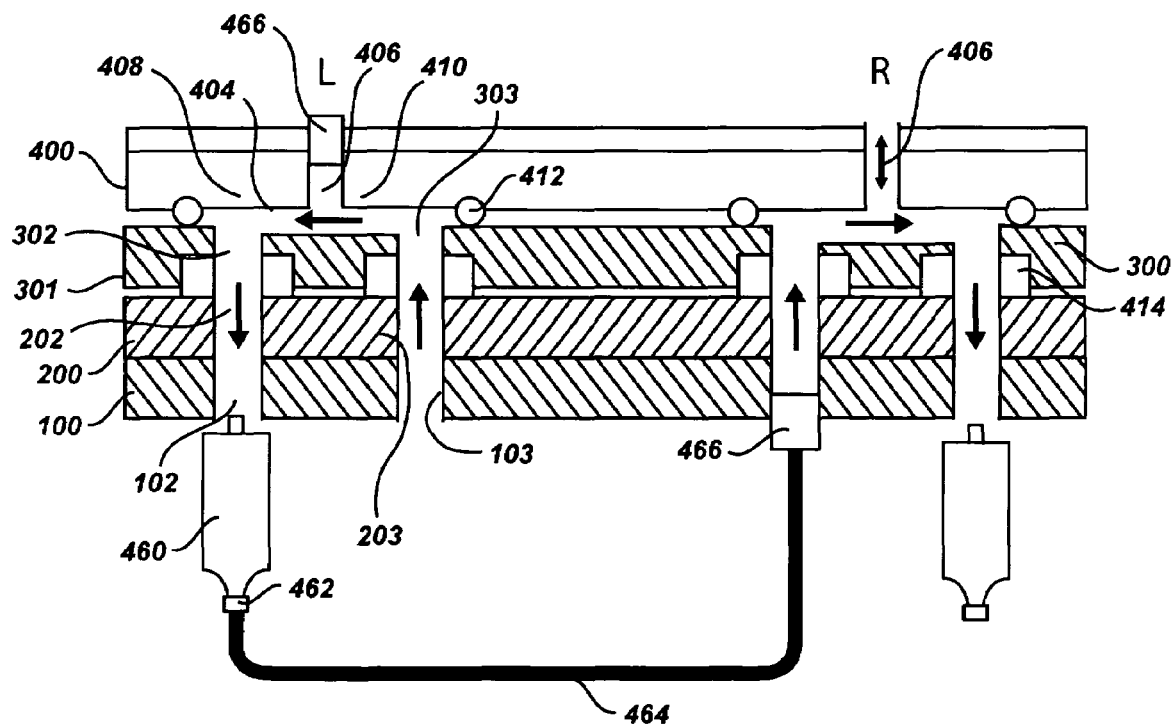
FIG. 4 is a cross-sectional planar view of the valve components. Note that the interconnections between columns are hypothetical, as in cross-section normally one column would be connected to the next in indexed position, not the column immediately opposite radically.

In a second preferred embodiment, cross-over liquid transfer is accomplished by a fourth top plate. FIG. 3*a* shows the spatial configuration of a top plate 400 in relation to the other parts of the rotary valve assembly. FIG. 5*c* illustrates the top plate 400 in greater detail. The lower surface 402 has a series of grooved recesses 404 arranged radially and within each grooved recess is a bore 406 extending through the top plate 400 to the upper surface. The grooved recesses 404 are positioned so that when the valve components are assembled in alignment, the interfacing plate 300 arrays of bores i.e. 302 and 303 (FIG. 3*b*) are disposed in alignment with the ends of the grooved recesses 408 and 410 (FIG. 5*c*). FIG. 5*c* also shows a plurality of bores 416 to which the stationary interfacing plate 300 thereby eliminated the need for bracing means as in the first embodiment. Referring to FIG. 4, the relationship of the valve components with respect to the spaces therein is visualized in a hypothetical cross-sectional view. The first plate 100, rigid plate 200, interfacing plate 300, and top plate 400 are shown in operating sandwich configuration, a seal between rigid plate 200 and interfacing plate 300 interceded by the gasket 414. The bores 102, 202, 302 and bores 103, 203, and 303 are shown in indexed alignment, terminating in the groove recess 404 at its ends, which forms a liquid communicating channel. Arrows mark the direction of flow in the illustration. Liquid entering bore 102 travels up through the valve body, across the communicating channel formed between the grooved recess 404 and the bottom of the top plate 400, and back down in the direction of a column 460. Eluent from the base of the column 460 flows through a conduit 464 into a second cross-over, and into a second column. In FIG. 4, the left cross-over (designated "L") is depicted with a bore 406 having in its upper portion, a plug 466. In the right cross-over (designated "R"), a bore 406' is shown open with a downward arrow indicating an inflow (desorbent or feedstock) of liquid to the system.

Referring again to FIG. 5*c*, one cross-over channel at the five o'clock position has been eliminated, and two compressible o-rings 414 have been substituted therefor, completely interrupting inter-column flow at this position. In operation, the interrupted position is exactly one index position clockwise from the intended entry site 420 for inflow of desorbent, thereby preventing any backflow and potential premature addition of desorbent to the system, (assuming counterclockwise rotation of column beds relative to valve positions). The interrupted flow ensures that selectively adsorbed substances will be released in the smallest possible volume of liquid extract, which improves purity and quantitative recovery. Similarly, backflow of the feedstock inflow can be prevented by interrupted flow at the index position adjacent clockwise to it. Optionally, positions counterclockwise adjacent to raffinate and extract outflow ports can similarly be interrupted. The method of interrupted flow to enhance recovery and purity can be used in many types of SMB apparatus, and in combination with recycling loops and other purification strategies known to the art, provided that nominal flow rates are less than about 3 liters/hour. In the machine of the first embodiment, interrupted flow may be conveniently achieved by simply clamping off the appropriate transfer loop 310. Flow pressure is achieved by operating the input flows utilizing an inline pump, and also fluid pressure within the column series is maintained by an inline pump on the return side of the flow loop. In the case of small scale SMB devices, appropriately sized conventional peristaltic or diaphragm pumps are preferred. To maintain proper alignment the stationary interfacing plate 300 (FIG. 5b) is fastened to the upper plate 400 (FIG. 5c) via bolts or screws in alignment with countersunk bores 316 having a seating surface 317 (FIG. 5b), aligned with bores 416 (FIG. 5c) of the top plate 400.

The multi-port rotary valve is assembled into a machine for carrying out small scale SMB chromatography. The basic features of a machine include means for rotating the lower plate and rigid plate against the stationary plate, compressing means to ensure the valve components are under sufficient pressure to obtain a non-leaking sealing engagement, control means to maintain the valve parts in alignment, positioning means to accommodate the chromatographic columns to receive the correct inflows in a predetermined sequence in a sequence in which the columns physically move with respect to the valve means, means to direct column outflows to the correct destination, and means to add or remove liquid from the system. There are many possible mechanical variations of the configuration of the components necessary to carry out the basic machine functions. Herein is provided two major embodiments, but variations will be apparent to those skilled in the art.

Figure 7:
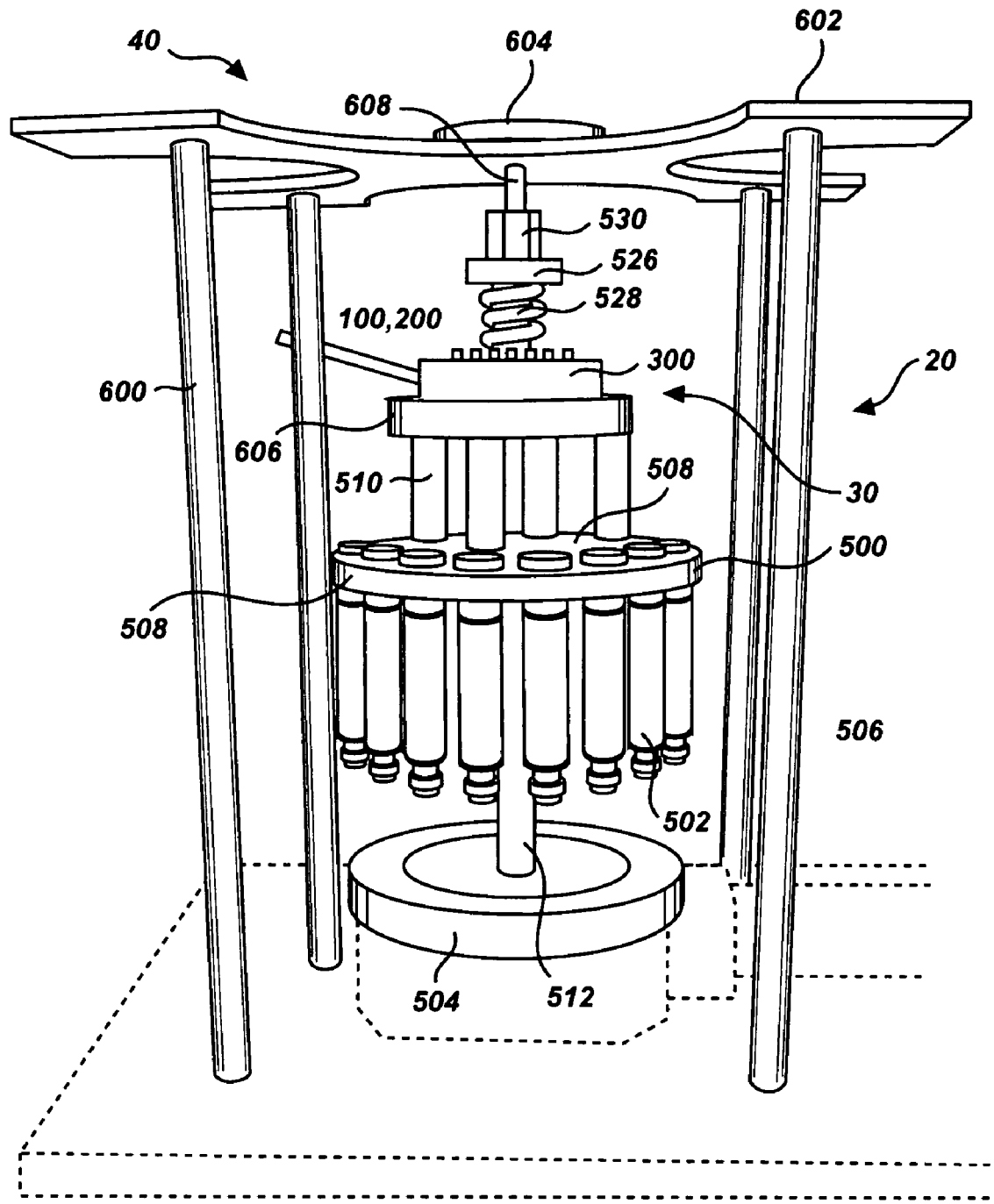
FIG. 7 is a perspective view of one embodiment of An SMB machine.

FIG. 7 depicts the assembly of parts comprising one embodiment of the present machine, generally designated 20. A plurality of chromatographic columns 502 are mounted circumferentially in a circular carousel, generally designated 500, comprising a rotatable inner frame base plate 504 anchored to a rotating shaft powered by a conventional drive train (dotted line structure), a plurality of support pillars 506 of equal length extending perpendicularly from the base plate 504, a yoke plate 508, a plurality of second tier support pillars 510 expending perpendicularly from the yoke plate 504, and valve assembly 30 mounted thereon.

Figure 8:
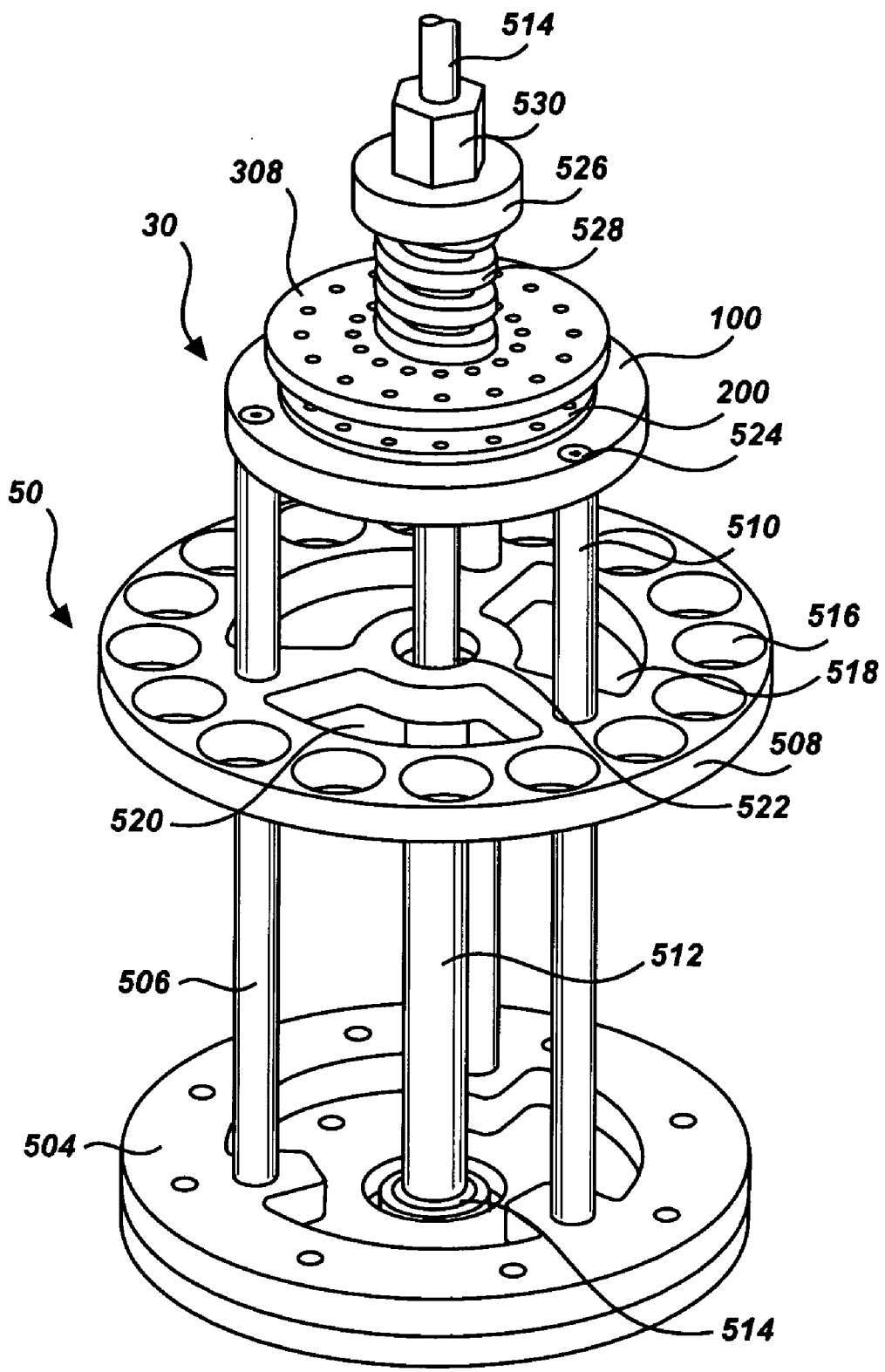
FIG. 8 is a perspective view of the central carousel apparatus of one embodiment of the invention, including partially exploded valve components.

FIG. 8, shows in greater detail the configuration of the carousel and support structures, generally designated 50, in relation to the valve assembly. An inner frame base plate 504 is shown with three support pillars 506 extending vertically to support a yoke plate 508, characterized in having a series of apertures 516 arranged radially around the perimeter of the plate. The yoke plate 508 is sized so that none of the valve assembly 30 obstructs vertical access to the carousel. Thus, columns of various lengths can be utilized. The apertures are sized so that inserted column has a diameter only slightly less than that of the aperture. Columns are retained in the apertures by their collars which conventionally have a somewhat larger diameter than the aperture. The carousel device has an advantage in that disposable columns may be easily and quickly changed without disassembling the machine. There is a central aperture 522 in the yoke plate 508, and one or more cut away portions 518 and 520 in the body of the yoke plate 508 to accommodate flexible conduits passing from the tops and bottoms of the columns to the valve assembly 30 thereabove. FIG. 8 also depicts the components of the valve in this embodiment, the rotatable first plate 100, the rigid plate 200, and the stationary interfacing plate 300. The interfacing plate 300 is maintained in stationary position by bracing means, typically cables extending between the outer surface of the interfacing plate and the support pillars of the outer support frame 600 (FIG. 7).

A central shaft 512 is anchored in a movable bearing 514 and extends perpendicularly from the inner frame support plate 504 through the central aperture 522 of the yoke plate 508, and further extends through the central apertures or alignment bores of the valve assembly 30. The portion of the central shaft 514' extending above the valve assembly 30 is characterized in having threads. A push plate 526 having compatible threads and a threaded locking nut 530 and threaded on the central shaft, threaded portion 514'. A spring 528 is disposed between the top plate 300 and the push plate 526. The push plate 526 and lock nut 530 are positioned so as to compress the spring 528, generating a downward pressure sufficient to establish sealing engagement amongst the valve assembly 30 components, 100, 200, and 300. This feature in a preferred embodiment ensures that the downward pressure exerted on the valve components is distributed uniformly to all parts of the valve component surfaces.

Referring again to FIG. 7, the SMB machine embodiment has an outer support frame, generally designated 40, comprising a plurality of support pillars 600 of equal height extending perpendicularly from any flat, sturdy surface. A outer frame plate 602 is mounted on the support pillars 600, and contains a central aperture 608 of sufficient diameter to receive the upper end of the central shaft 512. The support pillars 600 are of sufficient height to provide vertical clearance for the spring 528, threaded push plate 526, locking nut 530. A capping plate 604 crowns the shaft apparatus. In operation, the outer support frame 40 stabilizes the vertical alignment of the carousel and support structures 50, and the valve assembly 30, and by independently securing the vertical axis, ensures uniformity of the pressure distribution on the contact surface areas of the valve assembly 30.

In a second embodiment of the present machine in which the cross-over liquid transfer is accomplished at the interface of the upper surface of the interfacing plate 308' (FIG. 3b) and the lower surface of the upper plate 402 (FIG. 3b), the upper plate 400 performs the function of the outer support frame plate 602. Referring to FIG. 5, an inner frame base plate 702 is mounted on a motor powered shaft, having indexing controls. A plurality of support pillars 704 of equal height to a length exceeding the vertical dimension of the longest column in use and its pendant connectors, extend perpendicularly from fixed positions 703 on a base plate 702, culminating in the rotating first plate 100 mounted thereon. The rigid plate is fixedly mounted on the first plate 100, having a central aperture 204 (FIG. 3a), the first plate 100 and rigid plate 200 comprising the rotating portion of the valve assembly. A lower machine base plate 700 supports the centrally positioned rotating assembly, generally designated 60, and peripherally near the edges of the machine base plate 700 is a plurality of machine support pillars 704 of equal length extending perpendicularly to a distance at least as great as the vertical height of the mounted rigid plate 200. The machine support pillars 706 have threaded extensions 708 rising to a level higher than the entire valve assembly 10 (FIG. 3a) upper surface. Bores 418 (FIG. 5c) are aligned with the vertical threaded extensions 708 of the top plate 400 (FIG. 5c), so that when the top plate 400 is mounted thereon, it can be secured under downward pressure by a spring loaded nut threaded thereon, to maintain the valve assembly with sufficient force to maintain the valve assembly components in liquid sealing engagement.

Figure 6:
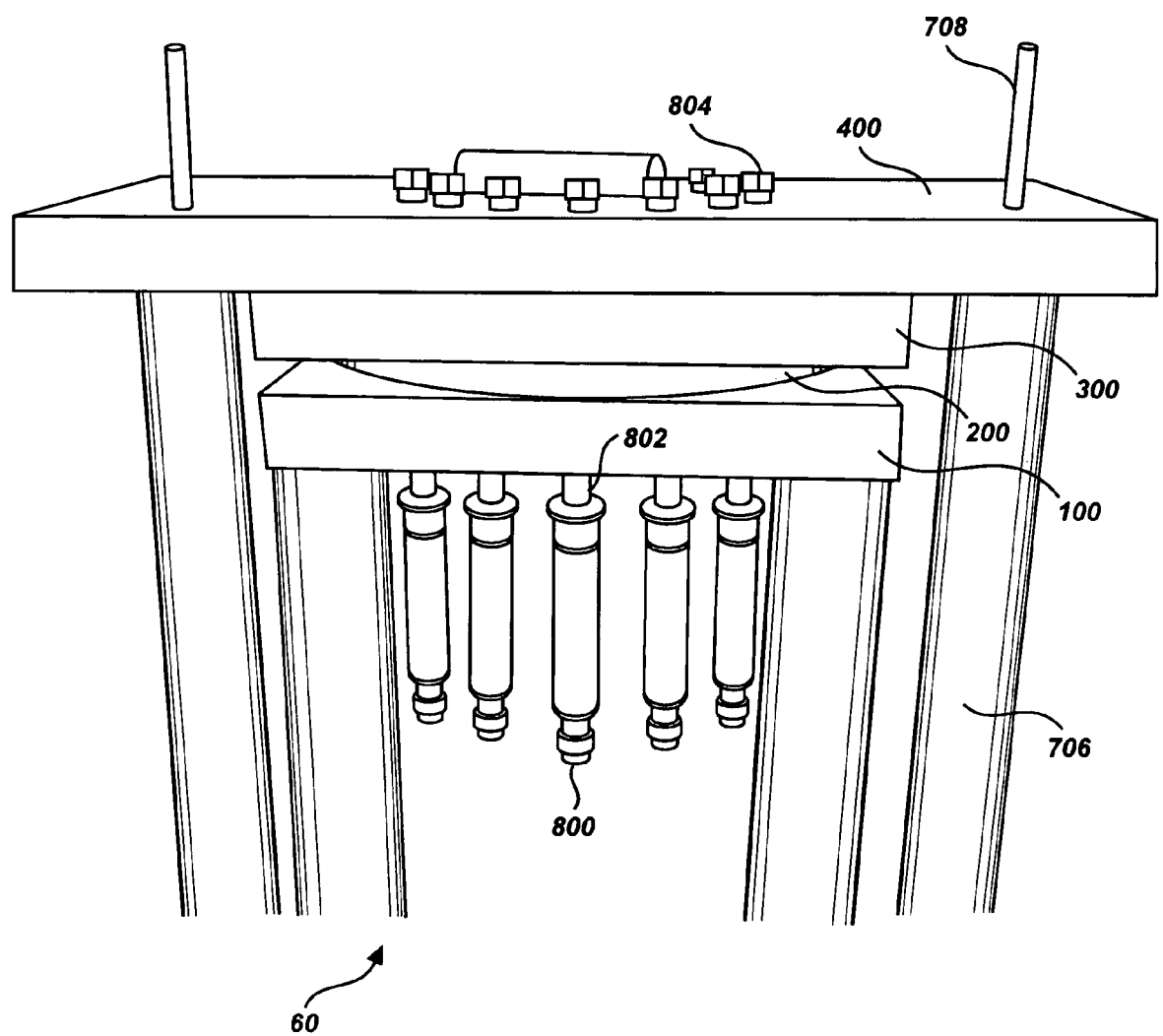
FIG. 6 is a perspective view of one embodiment of an SMB machine.

In this embodiment, the columns are limited in size for small scale SMB separations on the order of about 2 to 75 cubic centimeters in bed capacity, and are generally not of sufficient weight to require carousel support. FIG. 6 depicts such embodiment having the centrally rotatable assembly 60, an outer support having vertical support pillars 706, pillar threaded extensions 708, and the valve assembly components, first plate 100, rigid plate 200, stationary interfacing plate 300, and top plate 400 shown mounted on threaded pillar extensions 708. Columns 800 are shown in FIG. 6 to be mounted directly to the threaded portion of bores 102 (FIG.

3a) in the first plate 100 by mating of upper connectors 802 attached to the upper body of the columns 800 having compatible threads therewith.

Columns fitted with conventional Luer-type connectors may be utilized in the present invention. However, one objective herein is to provide disposable sorbent containing columns or cartridges, easily and quickly interchangeable with replacement units. Luer-type fittings have become a staple of the chromatography industry. However, they have one major disadvantage; namely, they require several turns which require unthreading connection/disconnection, and also wrapping the threads with a substance such as Teflon™ tape to ensure sealing.

Figure 9A:
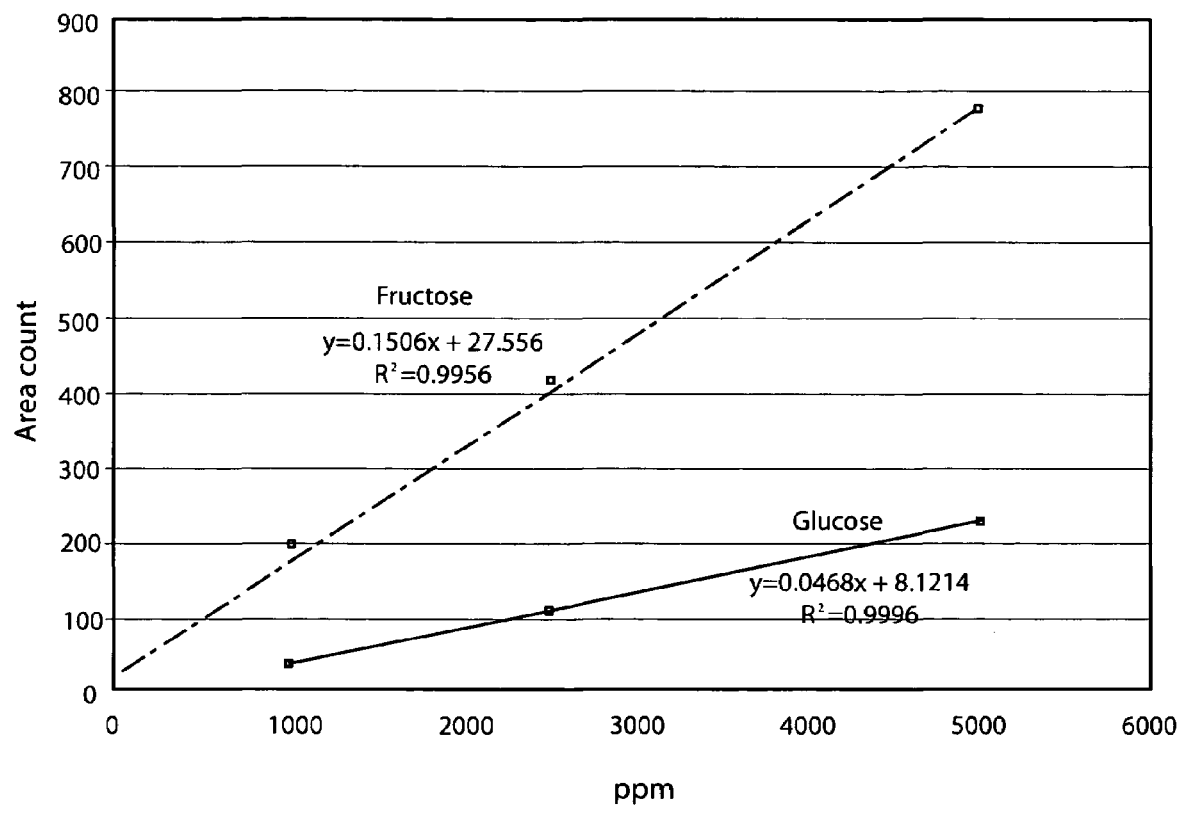
FIG. 9A, 9B and 9C is a planar drawing of two components of the quite disconnect connector device.
Figure 9B:
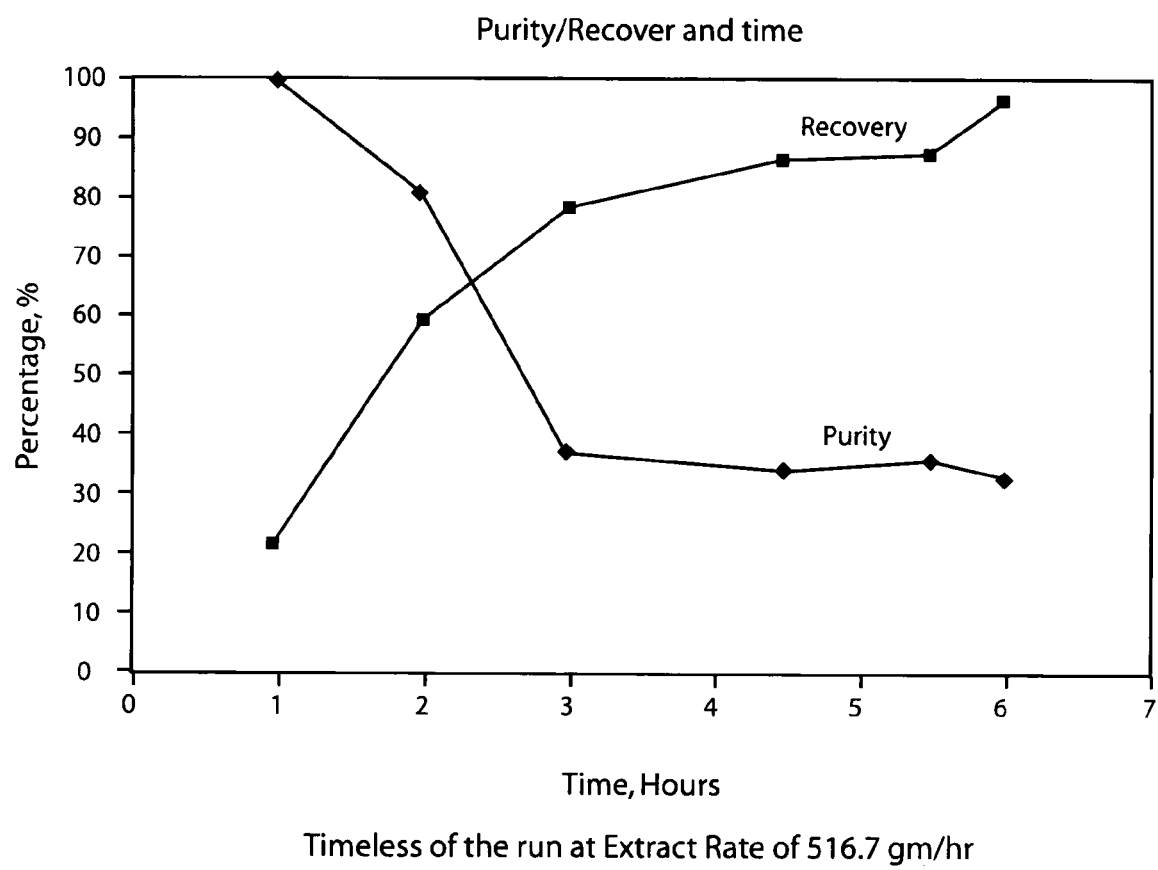
Figure 9C:
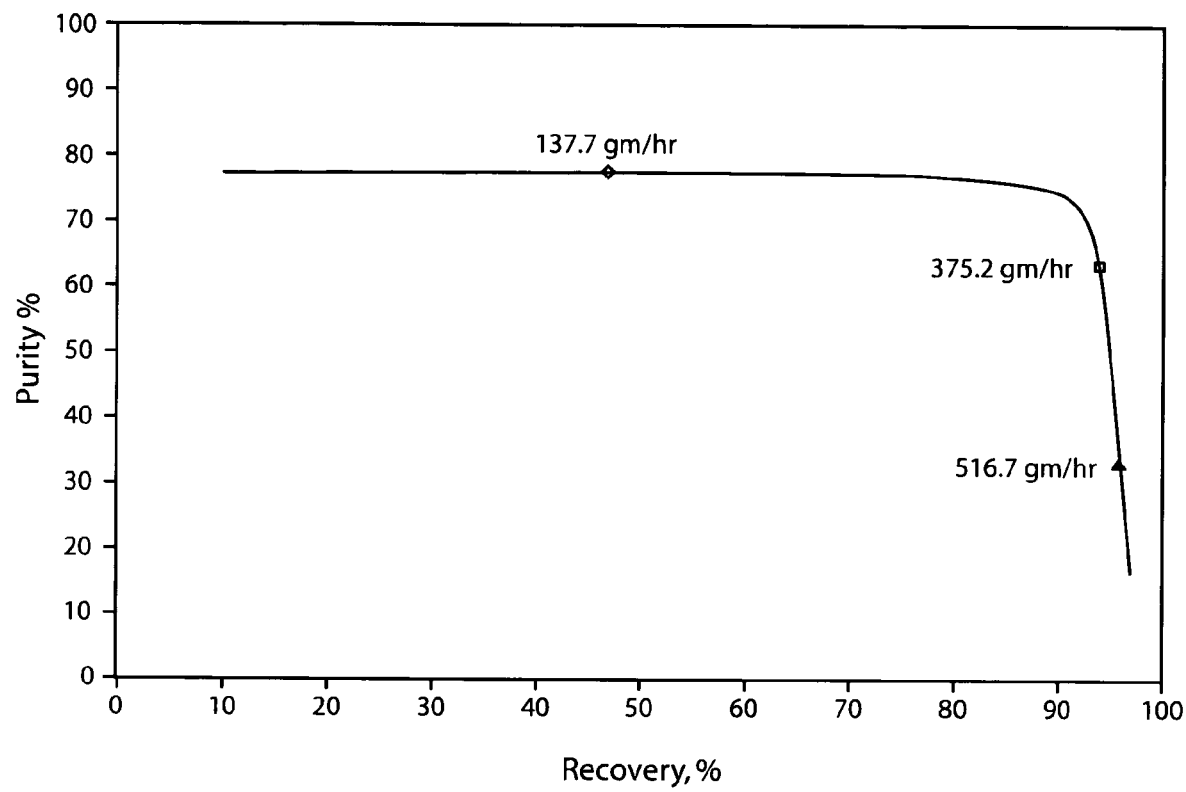

The present invention provides a quick disconnect fitting for column attachment to the valve assembly. Referring to FIG. 9, a disconnect fitting comprises a two part assembly, a female portion 900 having a cylindrical molded body with an outer surface 903 having an upper cavity 905 containing a tapered nipple member 906 extending upward out of the cavity 905, and having a central communicating bore 902 extending downward through the entire body of the female portion 900. The inner wall 907 of the cavity 905 bears a groove thread 908 of not greater than one turn. A male portion 901 of the disconnect fitting comprises a cylindrical body 912 having a central bore 914 and a tapered central cavity 916 adapted to insert into the female portion upper cavity 905. The male portion 901 bears a plurality of tabular projections 910 mateable to the grooved thread 908 of the female portion 900. The female portion 900 of the quick disconnect fitting may be threaded so as to be accommodated by the threaded portion of first plate bores 102 (FIG. 3) of the SMB valve assembly. The male portion 901 may be adapted to a chromatographic column, preferably integral therewith, to provide means to install a new column in an SMB machine quickly, and without the need for Teflon sealing.

Other advantages of the present invention will be apparent from the following Example.

EXAMPLE

Experiments were conducted on a high fructose feedstock to measure separation efficiency of fructose and glucose utilizing an SMB chromatography as heretofore disclosed in the first embodiment. Sixteen columns containing approx. 150 cubic centimeters of packed Dowex Monosphere 99CA/320 ion exchange resin (Supelco) were installed in the machine, and allowed to equilibrate. Identification and quantitation of sugars in the extract and raffinate were carried out by HPLC on an HP 1090 liquid chromatograph, calibrated with pure glucose and fructose, under the following conditions: detection at 192 nm, HPLC column type Hypersil APS 5 micrometers, 150 mm×4.6 mm. The samples were diluted in water, acetonitrile in a 75:25 ratio. The mobile phase was 20:80 water-acetonitrile. The results are shown in FIG. 10a.

High concentration fructose (Archer Daniels, Midland No. 42) was introduced into the system as feedstock. The feed rate thereof and the desorbent rate were kept constant, and the extract rate was varied to generate a glucose fructose purity curve. Cycle time for indexed positions was maintained at 5 minutes. Table 2 summarizes the test conditions:

TABLE 2

| Feed rate, gm/hr | Desorbent rate, gm/hr | Extract rate, gm/hr |
|---|---|---|
| 160 | 1818 | 137.7 |
| 160 | 1818 | 375.2 |
| 160 | 1818 | 516.7 |

The feed and desorbent rates were measured on a hourly basis by weighing the amount left in the reservoir. The extract and raffinate were collected in flasks, which were weighed hourly to measure the flow rates. Samples were applied to the HPLC on an hourly basis to measure the concentration of glucose and fructose in the extract and raffinate. Purity was assessed as the fraction of fructose in the extract. Recovery was calculated as the ratio of the amount of fructose in the extract in the extract and the amount of fructose in the feedstock. Results depicted in FIG. 10b show that steady state recovery was achieved after an unstable period of approx 5-6 hours of operation. FIG. 10c shows the final purity vs. recovery curve.

What is claimed is:

1. A multi-port rotary valve assembly having structurally aligned components for simultaneously directing a plurality of liquid flows comprising
    a rotatable first plate having a plurality of partially threaded bores arranged in two concentric arrays of equal number, the number of bores in each said array being equal to the number of potential liquid flows
    a rigid plate composed of a fluorocarbon polymer having an inner and an outer surface, joined immovably at its inner surface to the side of the first plate opposite of said threads, said rigid plate being lapped on its outer surface to a flatness tolerance of not greater than 15 microns, and said rigid plate further having bores in corresponding spatially registered alignment to the bores of the first plate
    a stationary interfacing plate comprising an inner and an outer surface having bores partially threaded from the outer surface and disposed in registered alignment common to the bores of the first said plate and said joined rigid plate, said interfacing plate bearing on its inner surface a pair of continuous recesses providing cavities extending concentrically around the plate adapted to receive in said cavities a gasket, the area of resistance provided circumferentially by the size and shape of said recess perpendicular sides resistant to forward movement of rotation being sufficient to withstand deformation or displacement of such gasket, wherein the inner and outer array bores are centered in each corresponding recess; and
    a fabric entrained gasket material accommodated to the size and shape of said recesses, the thickness of the gasket being greater than the depth of said recess cavities, whereby to form a sealing engagement between the gasket and said rigid plate when the first plate and joined rigid plate are rotated against said stationary interfacing plate gasket under sealing pressure applied to the aligned valve assembly components; and
    means to apply uniform pressure across said plates so as to attain a hydraulic seal.

2. The multi-port rotary valve of claim 1, said valve being further characterized in having an additional top plate comprising an upper and a lower surface, the said lower surface having a series of grooved recesses arranged radially and containing a recess bore placed inside of said grooved recess and terminating in the upper surface of the top plate, the ends of said grooved recess configured to align with the inner and outer concentric array of bores in the interfacing plate when joined to said top plate, to form communicating channels within said recesses permitting flow between one inner and one outer bore, such flow being constrained by sealing means isolating each inner and outer bore pair.

3. The rotary valve of claim 2 adapted for use in a small scale simulated moving bed separation device, wherein four of the bores exposed on the outer surface of said interfacing plate are dedicated to feedstock inflow, raffinate outflow, desorbent inflow, and extract outflow, at positions selected by empirical determination of the substances to be separated, and either one or both of the bores indexed one position clockwise from said dedicated feedstock or desorbent inflow bores, and, zero one, or two of the bores indexed one position counterclockwise from said dedicated raffinate or extract bores are fitted with threaded blocking means mateable with said threaded bores so designated to prevent flow therein.

4. The rotary valve of claim 1, wherein the placement of said gaskets within said recesses is mechanical without chemical adhesion therebetween.

5. The rotary valve of claim 1, wherein the fluorocarbon polymer is substantially non-deformable under pressures of up to about 2000 ft lbs, and comprises a machinable grade of polymer selected from the group consisting of high density PTFE, ETFE, PCTFE, and related materials having lappable surfaces and high hydrophobicity.

6. The rotary valve of claim 1, wherein the rotatable first plate, the rigid plate, and the interfacing plate have a central alignment aperture.

* * * * *